MEDICINAL SKIN CREAM FOR PSORIASIS AND METHOD

BACKGROUND OF THE INVENTION

1. Field of the Invention

The present invention relates to medicinal skin creams and in particular to such a cream using acetohexamide as an active agent for the relief of psoriasis and related skin ailments.

2. Description of the Prior Art

Psoriasis is a chronic skin disorder characterized by reddish elevated areas or epidermal plaques usually covered with silvery-white scales. Neither the cause nor a permanent cure are known at this time. Numerous methods of treatment have been devised and a large number of skin ointments developed and marketed for the relief of this ailment. The most successful ointments are believed to have been ointments utilizing various tars, steroid hormones and/or mercury. Tars generally produce an unpleasant odor and undesirable skin coloration while continuous use of mercury and/or steroid hormones frequently elicits undesired side effects.

SUMMARY OF THE INVENTION

In accordance with the present invention it has been discovered that acetohexamide and a steroid hormone will coact so as to normally terminate the symptoms of psoriasis in an unusually short time. After original treatment in accordance with the invention, psoriasis symptoms either do not or are very slow in returning whereby further treatment is minimized and there are no undesirable side effects. The invention was discovered as a result of observing the reduction of psoriasis in a diabetic patient after commencing diabetic treatment with acetohexamide preparations administered internally.

DESCRIPTION OF THE PREFERRED EMBODIMENT

In the present invention a skin cream or ointment for relief of psoriasis and related skin ailments is prepared from acetohexamide and a steroid hormone derivative mixed in a cream base. Specific examples of the inventive skin cream are as follows:

EXAMPLE I

Five grams of acetohexamide (1-[(p-Acetylphenyl) sulfonyl]-3-cyclohexylurea) were mechanically mixed with 57 grams of 0.1% triamcinolone (9aFluoro-11B, 16a, 17, 21 tetrahydroxypregna-1, 4-diene-3, 20-dione) in a vanishing cream base.

EXAMPLE II

Five grams of acetohexamide were mechanically mixed with 57 grams of 0.1% triamcinolone acetonide (9a-Fluoro-11B, 16a, 17, 21-tetrahydroxypregna-1, 4-diene-3, 20-dione cyclic 16, 17-acetal with acetone) in a vanishing cream base.

Creams in accordance with the above samples were applied to severe cases of psoriasis in the following manner:

Thin application to the afflicted areas every eight hours for ten days. Complete remission of the ailment observed at the end of ten days. Recurrence is prevented by application to pink spots preliminary to lesions. Application three times a day until such spots disappear is normally a two day procedure.

The above regimen and results have been observed in 50 cases to date with no adverse side effects indicated. Similar results are indicated in 25 additional cases that have not yet been observed over the ten days plus a minimum three month observation period.

Identical treatments have been tried first without the acetohexamide and second without the triamcinolone. The same strength of the single ingredient was used in a vanishing cream base. Some relief was observed in these cases, but full remission was not attained and recurrence set in quickly on discontinuance.

While the invention has been described with relation to specific embodiments, other steroid hormone derivatives of similar characteristics would be applicable and the mixture proportions are not critical. Thus a mixture of 1 gram to 10 grams acetohexamide and 28 grams of 0.01% to 1% steroid hormone cream can be used. The strength of the mixture within these limitations will affect the number of required applications and total time for complete remission. Also, it can be anticipated that stronger mixtures may produce adverse side effects in some cases.

I claim:

1. A medicinal compound administered as a skin cream and comprising a mixture of 1 gram to 10 grams of acetohexamide to 28 grams of 0.01% to 1% steroid hormone cream taken from the group consisting of triamcinolone and triamcinole acetonide.

2. A medicinal compound according to claim 1 wherein said mixture is substantially 5 grams of acetohexamide to substantially 57 grams of approximately 0.1% triamcinolone in a vanishing cream base.

3. A medicinal compound according to claim 1 wherein said mixture is substantially 5 grams of acetohexamide to substantially 57 grams of approximately 0.1% triamicinolone acetonide in a vanishing cream base.

United States Patent [19]

DeLuccia

[11] 4,131,652
[45] Dec. 26, 1978

[54] MEDICINAL SKIN CREAM FOR PSORIASIS AND METHOD

[76] Inventor: Charles R. DeLuccia, 2 Maple Ave., Rye, N.H. 03871

[21] Appl. No.: 808,866

[22] Filed: Jun. 22, 1977

[51] Int. Cl.² ............................................. A61K 31/58
[52] U.S. Cl. ................................. 424/241; 424/243
[58] Field of Search ........................................... 424/241

[56] References Cited

U.S. PATENT DOCUMENTS 3,966,924  6/1976  Fredriksson ........................ 424/240

Primary Examiner—Elbert L. Roberts
Attorney, Agent, or Firm—Thomas N. Tarrant

[57] ABSTRACT

A coactive mixture of acetohexamide and a steroid hormone in a cream base and method for the relief of psoriasis and related skin ailments.

3 Claims, No Drawings